United States Patent [19]

Mehra

[11] Patent Number: 4,680,042
[45] Date of Patent: Jul. 14, 1987

[54] EXTRACTIVE STRIPPING OF INERT-RICH HYDROCARBON GASES WITH A PREFERENTIAL PHYSICAL SOLVENT

[75] Inventor: Yuv R. Mehra, Odessa, Tex.

[73] Assignee: Advanced Extraction Technologies, Inc., Houston, Tex.

[21] Appl. No.: 828,988

[22] Filed: Feb. 13, 1986

Related U.S. Application Data

[63] Continuation-in-part of Ser. No. 808,463, Dec. 13, 1985, which is a continuation-in-part of Ser. No. 784,566, Oct. 4, 1985, Pat. No. 4,617,038, which is a continuation-in-part of Ser. No. 759,327, Jul. 26, 1985, Pat. No. 4,623,371, which is a continuation-in-part of Ser. No. 758,351, Jul. 24, 1985, Pat. No. 4,601,738, which is a continuation-in-part of Ser. No. 637,210, Aug. 3, 1984, Pat. No. 4,578,094, which is a continuation-in-part of Ser. No. 532,005, Sep. 14, 1983, Pat. No. 4,526,594, which is a continuation-in-part of Ser. No. 507,564, Jun. 24, 1983, Pat. No. 4,511,381, which is a continuation-in-part of Ser. No. 374,270, May 3, 1982, Pat. No. 4,421,535.

[51] Int. Cl.⁴ .................................................. F25J 3/00
[52] U.S. Cl. .......................................... 62/17; 55/29; 55/68; 62/20
[58] Field of Search ................. 62/17, 20; 55/29, 68

[56] References Cited

U.S. PATENT DOCUMENTS

| | | | |
|---|---|---|---|
| 1,934,029 | 11/1933 | Asbury | 23/210 |
| 2,325,379 | 7/1933 | Durrum | 202/40 |
| 2,357,028 | 8/1944 | Shiras et al. | 202/67 |
| 2,433,286 | 12/1947 | McKinnis | 202/39.5 |
| 2,455,803 | 12/1948 | Pierotti | 202/39.5 |
| 2,521,233 | 9/1950 | Latchum, Jr. | 183/115 |
| 2,559,519 | 7/1951 | Smith et al. | 202/39.5 |
| 2,570,066 | 10/1951 | Morrow et al. | 202/39.5 |
| 2,596,785 | 5/1952 | Nelly | 48/190 |
| 2,663,169 | 12/1953 | Twomey | 62/175.5 |
| 2,814,359 | 11/1957 | Koble | 183/115 |
| 3,097,924 | 7/1963 | Kinney et al. | 23/209 |
| 3,197,970 | 8/1965 | Nelson et al. | 62/17 |
| 3,202,482 | 8/1965 | Herster | 23/209 |
| 3,213,151 | 10/1965 | Sherk | 260/667 |
| 3,280,206 | 10/1966 | Scola et al. | 260/674 |
| 3,349,145 | 10/1967 | Uitti | 260/672 |
| 3,383,838 | 5/1968 | Carson | 55/44 |
| 3,455,116 | 7/1969 | Swift et al. | 62/17 |
| 3,616,271 | 10/1971 | Copelin | 203/52 |
| 4,158,556 | 6/1979 | Yearout | 62/28 |
| 4,511,381 | 4/1985 | Mehra | 62/17 |

OTHER PUBLICATIONS

"Ethylene Purification by Absorption Process", by Kniel and Slager, *Chemical Engineering Progress*, vol. 43, No. 7, Jul. 1947, pp. 335-342.

"Propane Recovery by Absorption," by Ludwig Kniel in *Petroleum Refiner*, vol. 27, No. 11, Nov. 1948, pp. 108-113.

(List continued on next page.)

*Primary Examiner*—Ronald C. Capossela
*Attorney, Agent, or Firm*—Depaoli & O'Brien

[57] ABSTRACT

A natural gas stream containing more than 3 mol percent of inert gases is extractively stripped with a preferential physical solvent to separate the inert gas from the $C_1+$ hydrocarbons and to separate selected amounts of $C_2+$, $C_3+$, $C_4+$, or $C_5+$ hydrocarbon product from a $C_1$ gas product which may additionally contain one or more of unselected $C_2$-$C_4$ hydrocarbons. The extraction and stripping are performed within at least one Extractive Stripping (ES) column which has a reboiler at its bottom, receives a stream of lean solvent at its top, and receives feed near its middle. When two ES columns are utilized, inert gas and methane may be recovered within the first ES column as overhead, and rich solvent may be withdrawn as its bottoms. The overhead may be separated in the second ES column into inert gas and methane. The rich solvent is regenerated by distilling in a product recovery column. It is also feasible to employ separate solvent systems, in which different solvents are used, in each ES column. The first ES column may alternatively be utilized for initially isolating the inert gas from the rich solvent containing all of the hydrocarbons. The rich solvent is fed to the second ES column for separating $C_1$ from a second rich solvent containing $C_2+$ hydrocarbons. This $C_2+$ rich solvent is fed to a hydrocarbon product column for separating lean solvent from the $C_2+$ hydrocarbons.

37 Claims, 5 Drawing Figures

OTHER PUBLICATIONS

"Le Calcul des Absorbeurs a Fractionnement," by L. Kniel in *Bulletin de l'Association Francaise des Techniciens du Petrole*, No. 82, Aug. 1950, pp. 31-56.

"Petroleum Processing—Principles and Applications," by R. J. Hengstebeck, McGraw-Hill Book Co., New York, New York, 1959, pp. 56-64.

"Humble's Avery Island Plant: High Safety at Low Cost", by J. J. Weatherby, *Hydrocarbon Processing & Petroleum Refiner*, Apr. 1962, vol. 41, No. 4, pp. 113-116.

"Gas Absorption", as Chapter 8 in Mass Transfer Operations, by Treybal, McGraw-Hill Book Company, Second Edition, 1968, pp. 221-226 and pp. 393-395.

"Chemical Engineers' Handbook", Ed. by John H. Perry, McGraw-Hill Book Company, Fourth Edition, 1969, pp. 13-46 and 13-47.

"High $CO_2$-High $H_2S$ Removal with Selexol Solvent," by John W. Sweny, 59th Annual GPA Convention, Mar. 17-19, 1980, Houston, Texas.

"Gas Conditioning," under Natural Gas in vol. 11 of *Kirk-Othmer Encyclopedia of Chemical Technology*, Third Edition, 1980, pp. 638-641.

"Absorption" under Liquified Petroleum Gas in vol. 14 of *Kirk-Othmer Encyclopedia of Chemical Technology*, Third Edition, 1980, pp. 383-388.

*Gas Processors Report*, Texas Coast, Spears Consulting Group, P.O. Box 33002, Tulsa, OK 74153, Oct. 14, 1985, pp. 1, 7 and 8.

EXTRACTIVE STRIPPING OF INERT-RICH HYDROCARBON GASES WITH A PREFERENTIAL PHYSICAL SOLVENT

RELATED APPLICATIONS

This is a continuation-in-part of co-pending application Ser. No. 808,463, filed Dec. 13, 1985 of Yuv R. Mehra, which is a continuation-in-part of co-pending application Ser. No. 784,566, filed Oct. 4, 1985, now U.S. Pat. No. 4,617,038, which is a continuation-in-part of co-pending application Ser. No. 759,327, filed July 26, 1985, now U.S. Pat. No. 4,623,371 which is a continuation-in-part of co-pending application Ser. No. 758,351, filed July 24, 1985, now U.S. Pat. No. 4,601,738, which is a continuation-in-part of co-pending application Ser. No. 637,210, filed Aug. 3, 1984, now U.S. Pat. No. 4,578,094, which is a continuation-in-part of application Ser. No. 532,005, filed Sept. 14, 1983, now U.S. Pat. No. 4,526,594, which is a continuation-in-part of application Ser. No. 507,564, filed June 24, 1983, now U.S. Pat. No. 4,511,381, which is a continuation-in-part of application Ser. No. 374,270, filed May 3, 1982, now U.S. Pat. No. 4,421,535.

BACKGROUND OF THE INVENTION

1. Field of the Invention

This invention relates to the treatment of gaseous streams containing appreciable quantities of an inert gas, such as nitrogen. It more closely relates to removing and recovering methane and higher boiling hydrocarbons from a gas stream, natural or synthetic, which contains large quantities of nitrogen or hydrogen, may contain acidic components such as $CO_2$ and $H_2S$, and may vary in moisture content from dry to saturated. It specifically relates to the removal of inert gases, such as nitrogen, from a gas stream in order to upgrade its heating value. It more specifically relates to adapting the extractive stripping embodiment of the Mehra Process for processing of gas streams containing hydrocarbons and contaminated with an inert gas. It additionally relates to purification of the lean solvent stream.

2. Review of the Prior Art

Many natural gases are contaminated with one or more inert gases which lower their Btu content or otherwise impair their marketability. Such inert gases include nitrogen, helium, argon, and, under ambient conditions, hydrogen in combination with alkanes and similar gaseous compounds of low reactivity. Refinery and petrochemical gaseous treatment products, containing relatively large amounts of hydrogen and highly reactive compounds such as olefins, are specifically excluded from the gases hereinafter under consideration.

During recent years, there has been strong emphasis on the secondary and tertiary methods of recovering oil from formations where the primary oil-producing methods are no longer productive. Nitrogen injection for reviving these oil wells is not useful in most formations, but in some formations such as in the central Texas area, nitrogen injection has been successfully utilized for the recovery of additional oil.

After several years of nitrogen injections at high pressure, approximately 2000 psig, the nitrogen seems to have broken through the formations in many instances. In other words, nitrogen is coming out with the oil and it is separated from the oil at the separator. Previously, the associated gases were rich in hydrocarbons heavier than methane, along with substantial quantities of methane. The present dilution effect of nitrogen has caused the same associated wellhead gas to have an extremely low BTU content, thereby making it unsuitable for pipeline shipments. If the natural gas contains more than 3% of nitrogen, it is off specification for most of the world's pipelines.

This situation has caused the oil producer to curtail oil production because he cannot burn the nitrogen-rich gas, and environmental laws prohibit him from venting the associated hydrocarbons. The oil producer is thus limited to the choice of technology available to him for properly processing the associated gases from an oil well. The available technology involves cryogenic principles, thereby causing the purified gas to be uneconomical in the natural gas market, even after subsidization with the revenues from oil production.

Natural gas is a mixture of hydrocarbons, including methane, ethane, propane, and various amounts of higher molecular weight hydrocarbons together with nitrogen and acid gases, such as $CO_2$ and/or $H_2S$. A "dry" gas is one containing predominantly methane with some ethane, propane, and butane and having a very low hydrocarbon dew point. The heavier the hydrocarbons, such as pentane and higher homologs, that are present in the gas, the higher the hydrocarbon dew point. For pipeline transmission, enough of the heavier hydrocarbons must be removed to lower the dew point without losing too many BTUs to meet specifications. In the past, gas with large quantities of high molecular weight hydrocarbons have been passed through gasoline extraction plants and/or dew point control stations to lower the dew point. Also, frequently the gas has required conditioning to remove sulfur compounds and carbon dioxide.

A nitrogen-rich gas stream, which can vary in composition from 3 to 75 mol. % nitrogen, the remainder being hydrocarbons, and from entirely dry to water saturated and from sweet to sour, can be extracted according to the extractive flashing embodiment of the Mehra Process in at least one and, if necessary, up to eight gas-extracting steps with a preferential physical solvent to provide up to three products, namely: a nitrogen gas product, a $C_1$-rich gas product, and a $C_{2+}$ liquid product, as taught in U.S. Pat. No. 4,623,371, which is incorporated herein by reference. The process upgrades the Btu value of a nitrogen-rich natural gas stream, for example, by extracting $C_1+$ hydrocarbons from the gas and then selectively separating the extracted products from the rich solvent by flashing to produce a $C_1$ rich gas stream with minimal amounts of nitrogen and a $C_1$-lean gas stream which is compressed, cooled, and condensed and finally demethanized to provide the $C_{2+}$ liquid product.

In addition to separation of methane from nitrogen, this extractive flashing embodiment of the Mehra Process provides selective recoveries of ethane in amounts ranging from 2–98%, propane in amounts ranging from 2–99%, butanes in amounts ranging from 2–100%, and pentanes and higher molecular weight hydrocarbons in amounts ranging up to 100%. Under the heading, "New NGL Extraction Process", the extractive flashing embodiment of the Mehra Process is described on pages 7 and 8 of the Oct. 14, 1985 issue of the *Gas Processors Report*, P.O. Box 33002, Tulsa, Okla. 74153. However, profitability for this embodiment of the Mehra Process can be improved by simplifying process design and minimizing capital and maintenance costs. Such a process has been disclosed in U.S. Pat. No. 4,617,038 and Ser. No. 808,463 which are incorporated herein by reference.

This improvement comprises: (a) selectively extracting and then stripping the natural gas stream with a preferential physical solvent to produce a natural gas stream of pipeline specifications and a rich solvent stream containing ethane and heavier hydrocarbon components and then (b) distilling the rich solvent to produce the natural gas liquids and the physical solvent for recycling to the extractive stripping step.

There remains, nevertheless, a need for processing an inert-rich gas stream to provide an inert gas product, a $C_1$-rich gas product, and a selectively extracted $C_2+$ liquid product. The processes of Ser. No. 784,566 and of Ser. No. 808,463 are not designed for meeting this need.

The processes of the parent U.S. Pat. Nos. 4,421,535; 4,511,381; and 4,526,594; all of which are incorporated herein by reference, utilize preferential physical solvents for processing natural gas streams by extracting, flashing, compressing, cooling, and condensing the desired components for producing natural gas liquid products. Ser. No. 759,327 is particularly directed toward processing of nitrogen-rich natural gas streams in this manner. In contrast, the process of Ser. Nos. 784,566 and 808,463 utilizes an extractive stripping (ES) step and minimizes the need for flashing of the rich solvent stream to separate the desired components of a raw gas stream.

Extractive distillation is well known in the prior art and is characterized by condensation of the overhead stream and refluxing of at least a portion of the condensed materials therein. Extractive stripping, in contrast, utilizes no condensation of the overhead stream and instead has a complete flow through of gaseous and liquid products, without reflux.

The preferential physical solvents preferred for the process of Ser. No. 808,463 are rich in monocyclic $C_8$–$C_{10}$ aromatic compounds having methyl, ethyl, or propyl aliphatic groups and selective for ethane and heavier hydrocarbons components of the gas stream such that: (a) the minimum relative volatility of methane over ethane is at least 5.0 (thereby defining its improved selectivity toward ethane over methane) and in addition a solubility of ethane in the solvent of at least 0.25 standard cubic foot of gaseous hydrocarbons per gallon of the solvent (SCF/GAL) (thereby defining its hydrocarbon loading capacity), or, alternatively, a preferential factor of at least 1.25. The preferential factor for physical solvent selection is defined as a product of relative volatility of methane over ethane multiplied by the solubility of ethane in physical solvents, specified as standard cubic feet of ethane per gallon (SCF/gal). However, the ideal preferential physical solvent would have a selectivity toward ethane over methane of at least 10.0 and would simultaneously possess a hydrocarbon loading capacity of at least 3.0 SCF/GAL. This combination of minimum relative volatility and minimum solubility enables solvent flow rate variations and operating pressure variations to be selectively utilized for flexibly producing liquid products having selected hydrocarbon compositions.

U.S. Pat. No. 2,325,379 teaches a process for separating a liquid mixture of components by extractive distillation in the presence of a relatively high boiling selective solvent which may be a polar solvent.

U.S. Pat. No. 2,357,028 relates to extractive distillation of a liquid mixture with a highly selective solvent, such as phenol, furfural, sulfolane, toluene, xylene, and ethyl benzene. A volatility ratio or "alpha value" is defined and given as a direct measure of the selectivity of the solvent.

U.S. Pat. No. 2,433,286 is directed to extractive distillation of liquid hydrocarbon mixtures with paraffin hydrocarbons as the extraction solvent in a first extractive distillation to produce olefins plus diolefins in the rich solvent and in a second extractive distillation with unsaturated or aromatic hydrocarbons as the solvent at a higher temperature to produce olefins as the raffinate and diolefins in the rich solvent. Paraffins are distilled from the rich solvent of the first extractive distillation and diolefins are distilled from the rich solvent of the second extractive distillation.

U.S. Pat. No. 2,455,803 describes a process for extractive distillation of a vaporizable organic mixture with a solvent comprising (1) a selective solvent and (2) a mutual solvent for the selective solvent and the mixture. The selective solvent must have high selectivity which is frequently coupled with low solvent power, thereby tending to form two liquid layers within the extractor. The purpose of the mutual solvent is to maintain a single liquid phase. The presence of the solvents in the mixture must cause a greater change in the "escaping tendency" of one component of the mixture relative to that of the other components, "escaping tendency" being defined as the potential of one component to pass from one phase to another. Solvents such as furfural and phenol are named as those having preferential solvent power for aromatic over paraffinic hydrocarbons. Suitable mutual solvents are identified as methyl ketone, cyclohexanone, lactonitrile, morpholine, and aromatic hydrocarbons such as benzene, toluene, cumene, mesitylene, and the like.

U.S. Pat. No. 2,559,519 relates to fractionating a liquid mixture of close-boiling oxygenated compounds in the presence of a large excess of a glycol-ether by continuous fractional distillation in a column of practical size, including a primary rectification zone, a secondary rectification zone above the primary zone, and a stripping zone below the primary zone for countercurrent vapor-liquid contact under reboiling and refluxing conditions.

U S. Pat. No. 2,570,066 is directed to a method of segregating pure hydrocarbons from hydrocarbon mixtures by extractive distillation in the presence of an aromatic hydrocarbon solvent which is preferably a mono-cyclic aromatic hydrocarbon fraction boiling in the range between 365° and 750° F. Mono-cyclic aromatic hydrocarbons having 10 carbon atoms, exemplified by tetramethylbenzenes such as 1,2,4,5-tetramethylbenzene, 1,2,3,5-tetramethylbenzene, and 1,2,3,4-tetramethylbenzene, and further exemplified by 1,2,-dimethyl-3-ethylbenzene, 1,2-dimethyl-4-ethylbenzene, and the like, are preferred. Durene, isodurene, prehnitene, and mixtures thereof are especially beneficial. The ratios of solvent to feedstock may range from about 1:1 to about 20:1, about 5:1 being preferred.

U.S. Pat. No. 3,280,206 relates to liquid-liquid extraction with inert organic solvents such as carbon tetrachloride, chloroform, tetrahydrofuran, diethylene glycol dimethylether, and benzenoid hydrocarbons which are free of olefinic and acetylenic unsaturation and boil at a temperature which is below the boiling point of the high boiler, such as benzene, toluene, ethylbenzene, xylenes, mesitylene, biphenyl, the lower alkyl biphenyls, and the terphenyls, in order to remove high boiling polyphenyls which have been formed by exposure to heat and/or ionizing radiation of organic coolants and coolant-moderators in nuclear reactors.

U.S. Pat. No. 3,616,271 teaches an extractive distillation method of separating chloroform and/or ethyl acetate from vinyl acetate by using a hydrocarbon having a boiling point of 100°-250° C. as the extractive solvent. Alpha values, as the ratios of relative volatilities determined from equilibrium distillation data for 1% solutions of chloroform and ethyl acetate in vinyl acetate, are calculated and used for evaluating the solvent. The greater the alpha value, the more volatile are liquids being removed as a substantially pure stream from the top of the column while the less volatile liquids are separated together with the extraction solvent from the bottom of the column. Among suitable solvents are alkyl aromatic hydrocarbons such as xylene, triethyl benzene, n-butyl benzene, and mesitylene.

Inert-rich natural gas streams can be processed according to the disclosures of U.S. Pat. No. 4,617,038 and Ser. No. 808,463, provided that it is acceptable to separate only the methane and heavier hydrocarbons ($C_1+$) from the gas streams and to reject the inert gas contained therein. Such a process is shown in FIG. 1, wherein the undesirable gases, consisting primarily of nitrogen, leave the top of the Extractor-Stripper (ES) column while the rich solvent containing the desired components leaves the bottom of the ES column. The $C_1+$ hydrocarbons are then separated from the rich solvent as a gas stream (e.g., a suitable natural gas stream for sale before processing to remove selective $C_2+$ components) from the top of the hydrocarbon product column while the separated solvent is recycled to the ES column for reuse.

The processes of Ser. Nos. 784,566 and 808,463 are not designed to separate the $C_2+$ hydrocarbons from an inlet nitrogen-rich natural gas stream and additionally to Btu-upgrade the residue natural gas stream. There is therefore a need to provide a process that includes the benefits of the inert-gas isolating invention of U.S. Pat. No. 4,623,371 in U.S. Pat. No. 4,617,838 and Ser. No. 808,463, namely, lower capital and energy requirements along with simplification of process design, and that is also capable of processing nitrogen-rich gas streams according to desired economics of the market.

An example of pertinent market economics occurs under poor economic conditions when ethane price as petrochemical feedstock is less than its equivalent fuel price and when the propane price for feedstock usage is attractive. At such times, the operator of a natural gas liquid extraction plant, for example, is limited as to operating choice because he is unable to minimize ethane recovery and maximize propane recovery in response to market conditions. A process is therefore needed that would separate $N_2$ from a fuel gas consisting essentially of methane and ethane and from an NGL product consisting essentially of $C_3+$ hydrocarbons.

There is consequently a further need for an extractive stripping process wherein propane and heavier hydrocarbons can be extracted to any selected degree from a natural gas stream without the need to extract significant quantities of ethane. There is still further a need for an extractive stripping process wherein butanes and heavier components can be recovered to any selected degree from a natural gas stream at extremely high recoveries without the need simultaneously to recover propane and ethane from the natural gas stream. There is at times also a need for an extractive stripping process wherein pentanes and heavier hydrocarbons can be recovered to any selected degree from a natural gas stream at extremely high recoveries without the need simultaneously to recover ethane, propane, and butanes therefrom.

An additional problem that arises in such extractive stripping processes is caused by the presence of small amounts of cyclic compounds in the gas stream when the cyclic compounds have a higher boiling point (i.e., a higher molecular weight) than the solvent. Under such circumstances, the cyclic compounds tend to build up in the solvent and cause the solvent to lose its preferential characteristics. There is accordingly also a need to provide a process that can maintain the preferential nature of the solvent without interfering with the extractive stripping process.

SUMMARY OF THE INVENTION

It is accordingly an object of this invention to provide a process for treating an inert-rich gas stream containing natural gases, including methane, that will separate the inert gas from the natural gases and then isolate methane from the remainder of the natural gases.

It is another object to provide a process for separating an inert gas from a natural gas mixture by treatment with a preferential physical solvent in order to upgrade the specific Btu value thereof.

A further object is to provide a means for processing a $C_1+$ natural gas stream that is rich in one or more inert gases by utilizing a preferential physical solvent for selectively extracting ethane and heavier hydrocarbons from both methane and the inert gas and then again utilizing the physical solvent for extracting methane from the inert gas, thereby forming three separate streams which leave the process.

An additional object is to selectively extract $C_2$-$C_4$ hydrocarbons in accordance with daily changing market conditions to provide a residue gas stream, meeting pipeline specifications and having a selected composition, and a liquid product stream, having a selected composition.

It is yet another object to provide a process that produces an inert gas product, such as a nitrogen product, and a hydrocarbon product.

It is yet an additional object to provide a process having the capability of selectively using different preferential physical solvents for different applications.

It is a still further object to provide a process for selectively rejecting at least one undesired hydrocarbon, of the group consisting of ethane, ethane plus propane, or ethane plus propane plus butane, to a selected degree from the stream of $C_1$-rich natural gas.

These objectives are achieved, according to the principles of this invention, by a process utilizing at least one and, if necessary, three or more gas contacting steps for treating a sweetened and dried inert-rich gas stream which can vary in composition from 3 to 75 mol. % inert gas, the remainder being hydrocarbons. According to one embodiment herein termed partial hydrocarbon extraction, the first gas-contacting step is employed for selective removal by extraction of all component materials except the inert gas and methane, thereby selectively isolating the inert/$C_1$ gas stream from the $C_2+$ fraction. The remaining gas-contacting steps are for extraction of the methane, the major hydrocarbon component, from the inert/$C_1$ gas stream. The pressures of these extractions can vary between 200 and 1,300 psig.

According to another embodiment, herein designated as total hydrocarbon extraction, one gas-contacting step is employed for selective removal by extraction of all hydrocarbon component materials, thereby isolating and rejecting the inert gas; this step extracts the major hydrocarbon component because it also removes the methane. The remaining gas-contacting steps are for extraction of the $C_2+$ hydrocarbons, the minor hydrocarbon components, from the methane.

Both gas-contacting steps are performed in at least one Extractor-Stripper (ES) column on a sweet, dry raw gas comprising an inert gas. Each ES column comprises an extraction section and a stripping section therebelow. The sections are flow connected for gas and liquid. Specifically, a sweetened and dried raw gas stream is first countercurrently contacted with a preferential physical solvent. The gas enters the ES column at the bottom of the extraction section and flows upwardly while contacting lean preferential physical solvent which, after entering the extraction section at the top of the column, flows downwardly and countercurrently to the gas. The contact takes place over mass transfer surfaces, such as packing or distillation trays. The solvent leaving the bottom of the extraction section is rich in methane and heavier $C_2+$ hydrocarbons.

This downwardly flowing $C_1+$-rich solvent enters the stripping section of the ES column and continues to flow downwardly, while coming in contact with the upward-flowing stripped hydrocarbons from the reboiler at the bottom of the ES column. The stripped hydrocarbons consist primarily of undesired hydrocarbons, such as $C_1$ if the desired objective is recovery of $C_2+$ hydrocarbons, or $C_1$ and $C_2$ if the desired objective is the recovery of $C_3+$ hydrocarbons, and so forth, depending upon the desired recovery objectives.

The process of this invention for upgrading inert-rich gas streams comprises extractive stripping of the gas streams with a preferential physical solvent to produce an inert gas stream, a $C_1$ gas stream which additionally comprises from none to selected amounts of $C_2$–$C_4$ hydrocarbons, and a gas liquid product (HP) stream. The extractive stripping step may be done in a single extractive stripping (ES) column or in two or more ES columns to produce the inert gas stream and the rich solvent stream containing the $C_1+$ hydrocarbons or the $C_2+$ hydrocarbons.

If two ES columns are used sequentially for extractive stripping of the inlet gas stream, the second ES column may be operated with a preferential physical solvent that differs from the preferential physical solvent used in the first column. Each solvent may flow in a closed cycle, so that there are two rich solvent streams. Alternatively, both ES columns may be operated with the same solvent.

The preferred process for using the same solvent in two ES columns is to operate the first ES column with a reboiler to obtain, as its bottoms, a solvent stream rich in $C_2+$ hydrocarbons and to produce, as its overhead stream, a gas stream of inert gas plus methane which forms the feed for the bottom of the extraction section of the second column. Preferably, the second ES column is at a higher pressure than the first ES column, and the overhead gas stream from the first column is compressed to that higher pressure. The process can be operated with the solvent flowing sequentially through both columns or with the solvent flowing in a closed cycle for each column. In the latter situation, the closed cycles may be operated with different solvents.

In either situation, the second ES column is operated to produce the inert gas as the overhead stream and a $C_1+$-rich solvent stream as bottoms which may be flashed to the pressure in the first ES column, or to a lower pressure if desired, to produce methane as overhead and a flashed solvent stream which is returned to the top of the second ES column. The methane may pass through a power recovery turbine which may be axially connected to the compressor for the inert gas stream.

As an alternative to two ES columns, a single ES column, having a top section and a bottom section which are separated by a gas flow-through dividing plate, also known as the chimney tray, can be built. The rich solvent from the bottom of the upper section is sent to a flash vessel. This vessel is operated at a selected pressure to produce a $C_1$-gas product and a solvent stream which is pumped to the pressure of the bottom section and fed to its top, just beneath the dividing plate. In this arrangement, the bottom column operates essentially at the same pressure as the top section.

The rich solvent leaving the bottom of the single ES column is let down in pressure to a pressure level consistent with the operation of the hydrocarbon product (HP) column. This pressure level, which is always lower than the pressure level in the ES column, also obviates the need for a downstream compressor or pump. The rich solvent may be economically heated by heat exchanging before entering the HP column in order to lower the reboiler heat load and improve separation of hydrocarbons from the physical solvent.

The HP column is a typical fractionation-type column in which the selectively extracted hydrocarbons are separated from the preferential physical solvent. The desired hydrocarbons are recovered from the top of the HP column while the hot, lean solvent is taken off from its bottom. The temperature at the bottom of the HP column is selected to ensure the recovery of all desirable hydrocarbons and is no higher than the boiling point of the physical solvent at the operating pressure. In order to minimize the loss of the physical solvent with the $C_1+$ or $C_2+$ hydrocarbons, the upper part of the column is refluxed with the condensed hydrocarbons.

In order to minimize the energy consumption within this process, the hot, lean physical solvent, leaving the bottom of the HP column, is effectively utilized for heating the rich solvent feed to the HP column and for reboiling the ES column before returning to the top of the extraction section of the ES column as cool, lean preferential physical solvent.

When the solvent flows through a closed cycle for each ES column, the first ES column may be operated for partial hydrocarbon extraction to produce an overhead mixture of the inert gas and methane and a rich solvent containing a mixture of $C_2+$ hydrocarbons. The second column, to which the overhead mixture from the first column is fed, may be operated to split the mixture into inert gas and methane.

As an alternative process when the solvent flows through a closed cycle for each ES column, the first ES column may be operated for total hydrocarbon extraction to isolate the inert gas as overhead from the first vessel. The rich solvent contains the $C_2+$ hydrocarbons recovered as bottoms. It is fed to a hydrocarbon product column that regenerates the solvent as its bottoms and produces $C_1+$ hydrocarbons as its overhead which is partially condensed. The condensate is returned to the product column as reflux. If desired, the $C_1+$ hydrocarbons may leave the process as gas product. The uncondensed gases are fed to the second ES column for extractive stripping with a lean solvent which may be a different solvent. The overhead is $C_1$ gas product, and the bottoms are $C_2+$ rich solvent. The rich solvent is fed to a hydrocarbon product column that produces lean solvent as its bottoms and an overhead which is partially condensed. The condensate is returned to the column as reflux; the uncondensed gases which may be condensed, if so desired, are the $C_2+$ product.

The $C_1+$ hydrocarbons may alternatively be fed to a $C_2+$ extractive flashing recovery plant, as disclosed in U.S. Pat. No. 4,511,381, which can be operated with a solvent recycling system. The solvent may be the same solvent as in the first system or a different solvent having desired preferential characteristics as to k-value and loading capacity.

It is important to note that in the process described so far, there is no external recycle of any streams. Although extractive stripping is generally described and is preferred for this invention, it is satisfactory to use extractive distillation as the unit operation by means of which the hydrocarbons are separated from the inert gas and from each other. Furthermore, this process has been essentially reduced to a two-step process. Thus, the capital requirements of this process are essentially reduced over the earlier embodiment of the Mehra process, as described in U.S. Pat. Nos. 4,421,535, 4,511,381, 4,526,594, 4,578,094, 4,601,738, and 4,623,371, all of which are incorporated herein by reference.

This two-step version of the Mehra Process necessitates that the rich solvent, leaving the bottom of the ES column in which minor-component extraction is performed, contain only the specified amounts of the undesirable lighter components, such as $C_1$ in $C_2+$ products, in order to meet the HP specifications. In previous versions of the Mehra process, such specifications have been effectively achieved by selective extraction, by selective flashing, by selective recycle of flashed streams, and by selecting the operating pressure and temperature at the bottom of the demethanizing or stripping step. Because such a purity requirement has been combined with selectivity in a single ES column of this invention, wherein the selection capability of operating pressure is relatively unavailable because it is generally determined by the delivery pressure of the residue gas, only temperature flexibility at the bottom of a single ES column is available for meeting the required specification as to undesirable components because the other flexibility of flow rate of preferential physical solvent to the ES column is effectively utilized in meeting the selective recovery levels of desired $C_1+$ hydrocarbon components of the raw gas stream. However, if available, it is preferred to operate the ES column at as low a pressure as economically practical since the process of this invention does not require unusually high pressures for extraction of desirable components.

However, the selective recovery of $C_2+$ components may be controlled to some extent by variations in flow rates of lean preferential physical solvents within the extraction section of the ES column. Additional selectivity of this invention is provided by the reboiler and the stripping section in the bottom portion of the ES column. The selected reboiling temperature enables the column to produce the rich solvent stream, consisting essentially of only the economically desired hydrocarbons, and reject the economically undesired hydrocarbons. Instead of a reboiler, a stripping stream of inert gas or methane may be utilized for selective rejection of the undesirable hydrocarbons.

The rejected undesirable hydrocarbon stream, flowing upwardly through the stripping section of the ES column, includes some of the desirable hydrocarbons, which have been boiled off from the rich solvent in the reboiler, as it flows over the packing or trays of the ES column. The hydrocarbons leave the stripping section of the ES column and join the incoming raw gas stream to form a mixed gas stream which flows upwardly in the extraction section of the ES column, where lean physical solvent preferentially recovers any contained desired hydrocarbons according to mass transfer principles developed for distillation.

In summary, the extraction section of the ES column is used for extracting desired hydrocarbon components from the natural gas stream to form an extracted liquid at the bottom of the ES column, and the stripping section of the ES column is used for rejecting the undesired components from the extracted liquid. Under certain operating conditions and for certain HP specifications, it may become necessary to operate the ES column bottoms at temperatures high enough to become relatively energy inefficient. It may thus be economically viable and preferred to allow additional quantities of undesirable hydrocarbons to be present in the rich solvent leaving the bottom of the ES column. These contained undesirable hydrocarbons tend to lower the temperature at the bottom of the ES column and thus allow for an effective energy recovery loop composed of rich/lean solvent streams.

The contained undesirable hydrocarbons can be effectively removed by providing a single-stage intermediate flashing vessel, operating at a pressure consistent with the operating pressure of the HP column. The separated vapor stream contains all of the undesirable components along with some desirable hydrocarbons. This stream is compressed to the pressure levels consistent with the operating pressure of the ES column. The compressed vapors are recycled to the ES column for additional recovery of desirable hydrocarbons.

The operating pressure and the temperature conditions of the ES column can vary from 200 to 1300 psig and 0° to 600° F., respectively, 300–600 psig being a preferred operating pressure range for the first ES column and 400–900 psig being a preferred operating pressure for the second ES column if utilized. Similarly, the operating pressure and temperature at the bottom of the HP column can vary from 10 to 500 psig and 150° to 800° F., respectively. The preferred range of pressure for the HP column is 150 to 350 psig. The operating temperature at the top of the HP column is determined by the equilibrium conditions for the desired composition of the hydrocarbon liquid product that are consistent with the market conditions and the operating pressure of the column. The operating pressure of the HP column is selected such that the desired hydrocarbon can be condensed by reasonably available cooling media such as ambient air, cooling water, or warm level refrigerant. The bottoms temperature of the HP column is preferred to be equivalent to the boiling point of the physical solvent at the operating pressure in order to ensure maximum recovery of desirable hydrocarbons.

A preferential physical solvent is defined for the purposes of this invention as having a minimum relative volatility of methane over ethane of at least 5.0 (thereby defining its improved selectivity toward ethane over methane) and in addition a solubility of at least 0.25 standard cubic feet of gaseous hydrocarbons per gallon of the solvent (SCF/GAL) (thereby defining its hydrocarbon loading capacity), or, alternatively, a preferential factor of at least 1.25. The preferential factor for physical solvent selection for the Mehra Process is defined as a product of relative volatility of methane over ethane multiplied by the solubility of ethane in physical solvents, specified as standard cubic feet of ethane per gallon (SCF/gal). However, the ideal preferential physical solvent would have a selectivity toward ethane over methane of at least 10.0 and would simultaneously possess a hydrocarbon loading capacity of at least 3.0 SCF/GAL, so that its preferential factor is at least 30.0. This combination of minimum relative volatility and minimum solubility enables solvent flow rate variations and operating pressure variations to be selectively utilized in the Mehra Process for flexibly producing liquid products having selected hydrocarbon compositions.

For example, the relative volatility for methane with respect to ethane in the presence of dimethyl ether of polyethylene glycol (DMPEG) is 6.4, indicating that it is more selective toward ethane than many other absorption liquids. As other examples, N-methyl pyrrolidone (NMP) and dimethyl formamide (DMF) have relative volatilities of methane/ethane of 5.3 and 8.5, respectively. However, the solubility of hydrocarbons in NMP is 0.03 standard cubic feet per gallon (SCF/GAL) and in DMF is 0.04 SCF/GAL; these values are low when compared to 1.0 SCF/GAL for DMPEG. It is the combination of these factors that determines the effectiveness of physical solvents. In general, if a choice must be made, it is better to have a high relative volatility than a high loading factor, although high levels of both indicators are needed for really good performance in the Mehra Process.

Combined preferential factors are given in the following Table I for a common lean oil, NMP, DMF, mesitylene, a hypothetical solvent having minimum requirements for Mehra Process applications, DMPEG, and a hypothetical ideal solvent in the Mehra Process. These preferential factors are important because they inversely indicate the amount of solvent which is required, in terms of solvent flow rate, for a given recovery level of desirable hydrocarbons. In other words, as 6.4 is much greater than 0.16, the amount of NMP required is 40 times the amount of DMPEG required for the same performance.

benzene, o-xylene, m-xylene, p-xylene, and mixtures thereof, rich being defined as more than 15% by weight. These compounds boil in the range of 270°–425° F.

Suitable sources of these $C_8$–$C_{10}$ aromatic compounds are aromatic streams, such as in petroleum refineries that are rich in mixed xylenes, $C_9$ alkylaromatics, and other $C_8$–$C_{10}$ aromatics. These compounds boil in the range of 270°–425° F. and are stable at the process temperatures used in separating mixtures into useful fractions and/or components, such as in distillation, extractive stripping, and extractive distillation operations. Moreover, they are also hydrocarbons which can be left in the liquid products in trace amounts, without interfering with use of such products in gasoline, for example, so that purification of the liquid products is not needed.

A principal refinery source of $C_8$–$C_{10}$ aromatic feed streams may be found in catalytically reformed naphthas in which a $C_9$ heart cut or extract of the reformate is enriched in $C_9$ alkylbenzenes, a typical reformate containing as much as 57% trimethylbenzenes based on the total content of $C_9$ aromatics. The composition of a $C_9$ heart cut is typically about 2.5, 87.5 and 10 mole % of $C_8$, $C_9$ and $C_{10}$ aromatics, respectively. Other sources of $C_8$–$C_{10}$ aromatic feedstocks are derived from gasoline producing processes such as the conversion of methanol to gasoline, as described in U.S. Pat. Nos. 3,931,349, 3,969,426, 3,899,544, 3,894,104, 3,904,916 and 3,894,102, and the conversion of synthesis gas to gasoline as described in U.S. Pat. Nos. 4,096,163, 4,279,830, 4,304,871 and 3,254,023, all of which are incorporated by reference. A $C_7$–$C_9$ mixed aromatic feedstock also may be used and can be derived from various sources including petroleum refinery sources, pyrolysis of coal to produce coke, tar sands, etc.

In petroleum processing operations such as transalkylation, isomerization, and disproportionation, for example, the product streams so produced are further treated, by fractionation and the like, to obtain alkylaromatic streams which contain substantial quantities of alkylbenzenes such as toluene, xylenes, and trimethylbenzenes. A typical alkylaromatic fraction which may be obtained contains predominantly $C_7$ to $C_9$ hydrocarbons and is referred to as crude xylenes.

Refinery streams suitable as preferential physical solvents for the present process are $C_9$ alkylaromatics, a $C_7$ to $C_9$ mixture of alkylaromatics, or a $C_8$–$C_{10}$ mixture of alkylaromatics. The $C_9$ alkylaromatic hydrocarbons are characterized as mainly monocyclic aromatic compounds, such as alkylbenzenes, which have at least one

TABLE I

| SOLVENT | Preferential Factors Defining Preferential Physical Solvents for Mehra Process Applications | | | | | | |
|---|---|---|---|---|---|---|---|
| | NMP | DMF | LEAN OIL | MIN. | DMPEG | MESITYLENE | MIN. FOR IDEAL |
| Relative volatility ($\alpha$) | 5.3 | 8.5 | 2.5–4.8 | 6.0 | 6.4 | 6.9 | 10.0 |
| Solubility, SCF/gal., $\gamma$ | 0.03 | 0.04 | 0.2–1.0 | 1.00 | 1.0 | 4.2 | 3.0 |
| Preferential factor ($\alpha \times \gamma$) | 0.16 | 0.34 | 0.5–4.8 | 6.00 | 6.4 | 29.0 | 30.0 |

Suitable preferential physical solvents include aromatic streams in petroleum refineries and petrochemical plants that are rich in monocyclic $C_8$–$C_{10}$ aromatic compounds having methyl, ethyl, or propyl aliphatic groups, including mesitylene, n-propyl benzene, n-butyl alkyl group which preferably contains no more than 4 carbon atoms. The $C_9$ aromatic hydrocarbons include, for example, 1,2,3-trimethylbenzene (hemimellitene), 1,2,4-trimethylbenzene (pseudocumene), 1,3,5-trimethylbenzene (mesitylene), isopropylbenzene (cumene), 1,2-methylethylbenzene, 1,3-methylethylbenzene, and 1,4-methylethylbenzene.

The C$_9$ alkylaromatics for use in the present process are conveniently available as product streams from various petroleum processing operations, including gasoline producing processes such as the conversion of methanol to gasoline or the conversion of carbon monoxide and hydrogen (syngas) to gasoline. Catalytic reformates, for example, are particularly preferred since they are enriched in aromatics and the C$_9$ fraction can be readily separated from non-aromatics by extraction with aqueous glycols, typically a Udex unit. The typical composition of extracted C$_9$ reformate and the boiling points of the C$_9$ aromatics contained therein are shown below in Table II.

TABLE II
COMPOSITION OF C$_9$ AROMATICS IN EXTRACTED REFORMATE

| Compound | Boiling Point (°F.) | Freezing Point (°F.) | Wt. % (based on total C$_9$ aromatics) |
|---|---|---|---|
| API Gravity | — | | |
| IBP, °F. | — | | |
| EBP, °F. | — | | |
| Isopropylbenzene | 306 | −141 | 0.6 |
| n-Propylbenzene | 319 | −147 | 5.2 |
| m-Ethyltoluene | 322 | −140 | 17.4 |
| p-Ethyltoluene | 324 | −80 | 8.6 |
| 1,3,5-Trimethylbenzene (mesitylene) | 329 | −49 | 7.6 |
| o-Ethyltoluene | 329 | −114 | 9.1 |
| 1,2,4-Trimethylbenzene (pseudocumene) | 337 | −47 | 41.3 |
| 1,2,3-Trimethylbenzene (hemimellitene) | 349 | −14 | 8.2 |
| Indane | 352 | — | 2.0 |
| | | | 100.0% |

While the quality of crudes may affect the quantity and type of C$_9$ aromatics extracted from a naphtha reformate, about 57 wt. % of the total C$_9$ aromatics are trimethylbenzenes in which pseudocumene, mesitylene and hemimellitene are typically produced in the following ratios:
Pseudocumene=1
Mesitylene=0.18
Hemimellitene=0.20

The C$_9$ aromatics may be further characterized as having an initial boiling point range of 230°–280° F., an end boiling point range of 350°–425° F., and an API gravity of 35–60.

A useful, although not ideal, source of preferential physical solvent is primarily a mixture of seven to nine carbon atom alkyl aromatics which include C$_7$ and C$_8$ aromatics, such as toluene, ethylbenzene and xylenes, and C$_9$ alkyl-aromatics identified in Table II above. Such charge stocks may also be derived from catalytic reformates, pyrolysis gasoline, etc., by distillation and solvent extraction to separate aromatic compounds from aliphatics. Other sources of suitable charge stocks include crude xylene streams, which actually contain alkylaromatics having 7 to 9 carbon atoms, and effluents from toluene transalkylation reaction zones which contain benzene, xylene, C$_9$ aromatics, and aromatics heavier than C$_9$. Mixtures of toluene and C$_9$ alkylaromatics may also be employed. The composition of a typical C$_7$–C$_9$ reformate cut is shown below in Table III.

TABLE III

| Products: | Analysis wt. percent |
|---|---|
| Naphthenes | 0.15 |
| Benzene | 2.03 |
| Toluene | 19.69 |
| Ethylbenzene | 0.004 |
| Paraxylene | 12.04 |
| Metaxylene | 27.64 |
| Orthoxylene | 10.40 |
| p-Ethyltoluene | 0.02 |
| m-Ethyltoluene | 0.06 |
| o-Ethyltoluene | 0.01 |
| Mesitylene | 7.18 |
| Pseudocumene | 15.82 |
| Hemimellitene | 1.93 |
| Ethylxylenes | 0.13 |
| Durene | 1.19 |
| Isodurene | 1.43 |
| Prehnitene | 0.28 |

The C$_7$ to C$_9$ aromatic mixture may be further characterized as having an initial boiling point range of 150° F., an end boiling point range of 350° F., and an API gravity of about 40.

The process of this invention uses a preferential physical solvent for extracting ethane and heavier hydrocarbon components from a gas stream, such as a natural gas stream, at any desired ethane recovery from 2% to 98% while recovering 99+% of propane and all heavier hydrocarbons. Using the same solvent, the process of this invention can achieve any desired propane recovery from 2% to 99+%, while recovering 99+% of butanes and all heavier hydrocarbons without recovering more than 2% of ethane and generally less than 0.4% ethane.

This invention process produces a liquid hydrocarbon product having a composition which is selectively versatile rather than fixed, as in prior art processes. In consequence, the composition of this hydrocarbon product, as in the previously disclosed embodiments of the Mehra Process, can be readily adjusted in accordance with market conditions so that profitability of the extraction operation can be maximized at all times and on short notice. Such versatility is achieved by flexibility in operating additions and steps. Specifically, the operator must consider and selectively change or vary the flow rate of the preferential solvent with respect to the flow rate of the natural gas stream. The flow rate may be varied within the range of 0.001–0.5 gallon of solvent per standard cubic foot of natural gas, such as natural gas. The operator must additionally selectively vary the temperature at the bottom of the ES column.

Selectively rejecting methane, methane plus ethane, methane plus ethane plus propane, or methane plus ethane plus propane plus butanes takes place within the ES column or columns. Depending upon the liquid product specifications and the inlet natural gas composition, the rejecting of undesirable hydrocarbons occurs in accordance with the temperature at the bottom of the ES column. Essentially, the stripping section of the ES column functions much like the demethanizing or stripping step of the basic Mehra process because in the stripping section, emphasis is placed on keeping undesired lighter hydrocarbons from coming down the column. In the extraction section, in contrast, emphasis is placed upon keeping the desired heavier components from continuing up the column and exiting as a part of the residue gas.

When the gas stream contains small amounts of cyclic compounds having a higher boiling point than the solvent, they tend to build up in the solvent and can cause undesirable changes in process conditions. By removing and treating a very small slipstream of the solvent from the outlet of the regenerator or of the product column, where the solvent is quite hot, the solvent can be maintained in a desired condition of purity with respect to these cyclic compounds. The volume of the slipstream is a function of the proportionate quantity of cyclic compounds in the inlet gas stream and is also simultaneously a function of the quantity of the cyclic compounds in the regenerated solvent stream leaving the bottom of the fractionator or regenerator.

This slipstream is sent to a small heat exchanger to increase its temperature at a low pressure or preferably to a vacuum still in order to recover the solvent from the cyclic compounds. The solvent is condensed and returned to the solvent loop. The cyclic compounds are recovered and sent to the gas liquids product stream. This operation can be either batch or continuous. Alternatively, the slipstream is sent from the small heat exchanger to a flash tank wherein the solvent is flashed and the cyclic compounds are recovered as the residue.

DESCRIPTION OF THE PREFERRED EMBODIMENTS

Figure 1:
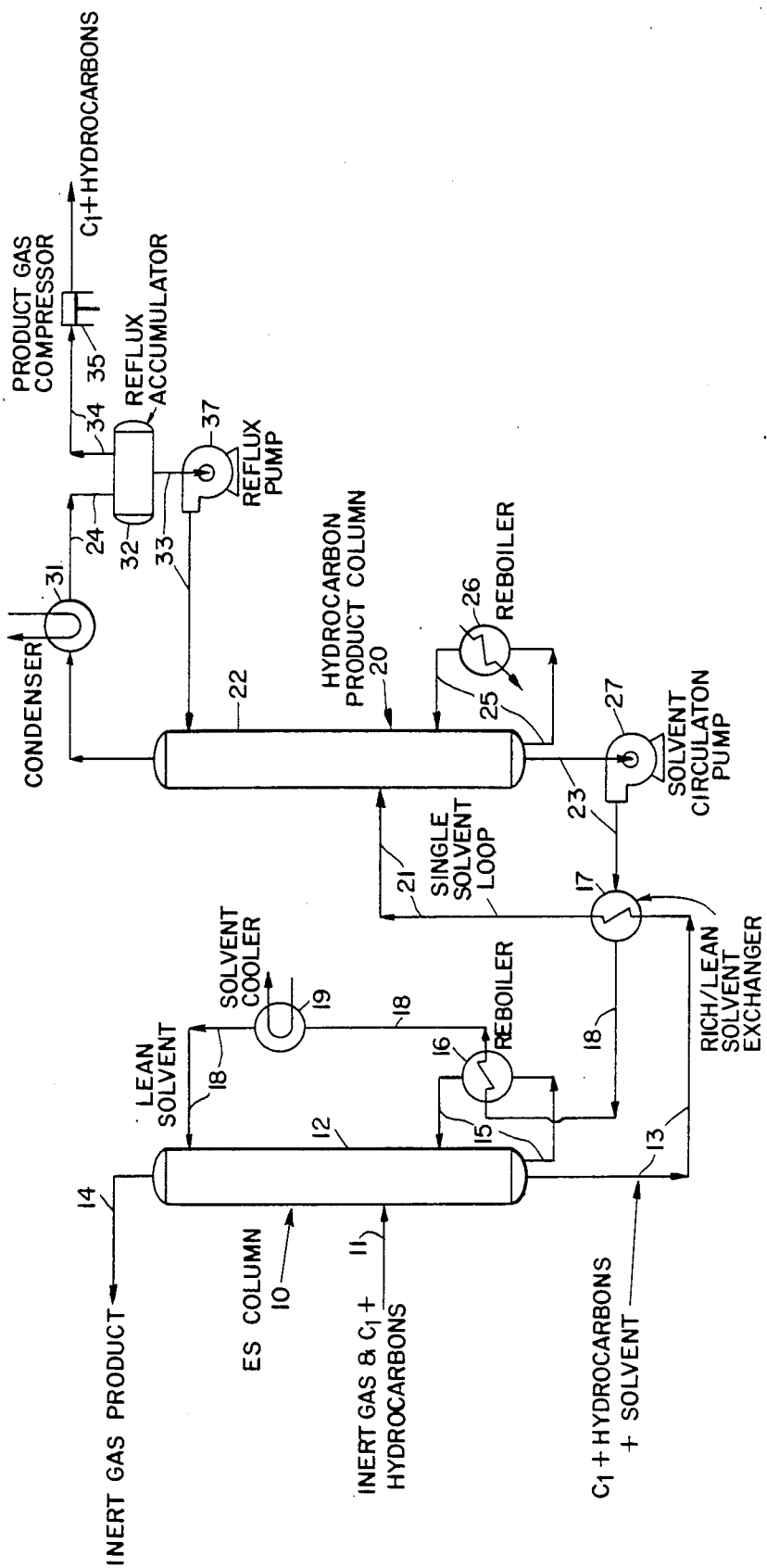
FIG. 1 is a schematic flowsheet for a two-column extractive stripping process in which a preferential physical solvent extracts $C_1+$ hydrocarbons from an inert gas-containing raw natural gas and then strips $C_1+$ hydrocarbons from the physical solvents while producing an inert gas product, such as $N_2$, $He_2$, and the like, and a $C_1+$ hydrocarbons gas product.

As shown in the drawings, the improved process of this invention for selective extraction of hydrocarbon liquids from a gas stream, which can be the extraction of natural gas liquids from a stream of dried and sweetened raw natural gas, comprises combined extraction and stripping within an Extractor-Stripper (ES) column to form a rich solvent and a residue gas, followed by distillation of the rich solvent to form the natural gas liquid product and lean solvent which is recycled to the ES column.

As shown in FIG. 1, the basic process for separation of inert gases (such as nitrogen) utilizes an Extractor-Stripper (ES) column assembly 10 and a hydrocarbon product column assembly 20. ES column assembly 10 comprises an ES column 12, a reboiler 16, a rich/lean solvent exchanger 17, and a solvent cooler 19. By definition, an extraction section of ES column 12 extends upwardly from the connection with line 11, and a stripping section extends downwardly therefrom.

A raw and sweetened inlet gas, containing an inert gas, such as nitrogen, and $C_1+$ hydrocarbons, is fed into ES column 12 slightly below its middle through line 11. The liquid at the bottom of column 12 circulates through line 15 and is heated in reboiler 16. Hot, lean solvent, which has been partly cooled in heat exchanger 17, passes through line 18 and reboiler 16 to heat the liquid in line 15, is cooled in solvent cooler 19, and enters the top of ES column 12. An overhead stream, containing nitrogen, for example, as the inert gas, leaves the top of column 12 through line 14. Rich solvent leaves the bottom of column 12 through line 13 and comprises solvent plus $C_1+$ hydrocarbons.

This stream passes through rich/lean solvent exchanger 17 and enters column 22 slightly below its middle through line 21. Liquid in the bottom of column 22 is heated by circulating through line 25 and reboiler 26 and returns to column 22. Liquid bottoms leave column 22 through line 23 and pump 27 to be cooled in exchanger 17.

An overhead vapor stream in line 24 is condensed in condenser 31 and is fed to reflux accumulator 32 from which condensed liquid leaves through line 33 and is returned as reflux by reflux pump 37 to the top of column 22. Uncondensed natural gases leave the top of reflux accumulator 32 through line 34 and are compressed by compressor 35 to form the $C_1+$ hydrocarbons product.

Alternatively, complete condensation of hydrocarbon vapors in condenser 31 is feasible, but use of energy is optimized by partial condensation. At the operating pressure, the low boiling $(C_2+C_3)$ portion of the hydrocarbon vapors in line 24 determine what the condensation temperature will be. The more $C_2$ it is desired to recover, the lower the condensation temperature must be.

Figure 2:
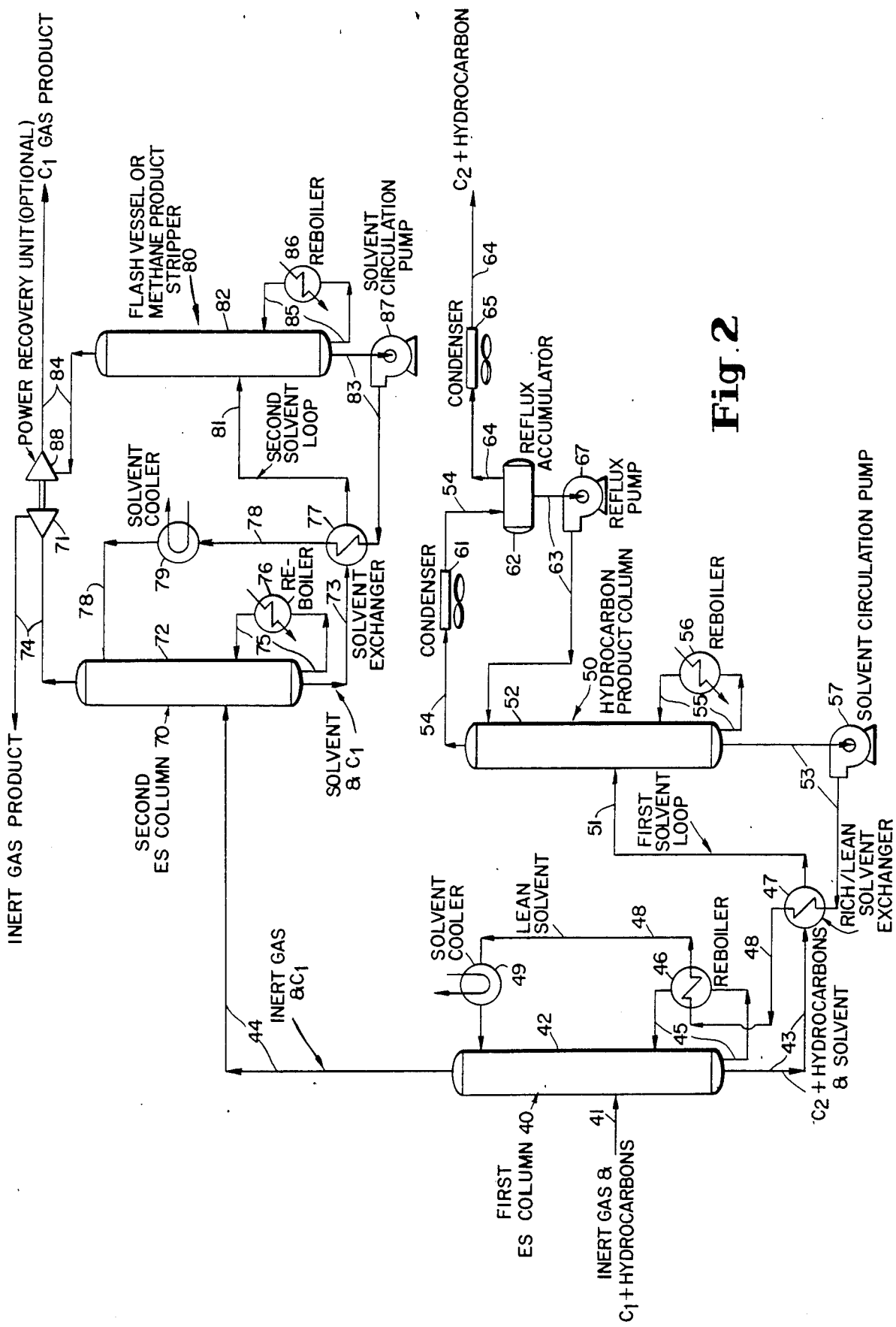
FIG. 2 is a schematic flowsheet for a extractive stripping process in which the first column separates the inert gas and methane from the remainder of the natural gases and the second ES column separates the inert gas from the methane.

FIG. 2 shows an inert gas separation process that is more complicated and more selective than the process of FIG. 1. The process of FIG. 2 utilizes first ES column assembly 40, hydrocarbon product column assembly 50, second ES column assembly 70, and methane product stripper assembly 80.

An inert gas-containing raw inlet gas, which has been sweetened and dried, enters column 42 slightly below its middle through line 41. Liquid at the bottom of column 42 circulates through line 45 and reboiler 46 to be heated. Hot, lean solvent, which has been cooled in rich/lean solvent exchanger 47, passed through line 48, cooled in reboiler 46, and cooled again in solvent cooler 49, enters the top of first ES column 42 to flow downwardly and countercurrently to the rising inlet raw gas. Bottoms leave the column through line 43 and are heated in rich/lean solvent exchanger 47. An overhead gas mixture of inert gas and methane leaves the top of column 42 through line 44.

The rich solvent heated in solvent exchanger 47 passes through line 51 to column 52 wherein the vapors rise through the rectification portion of this column, countercurrently to refluxed hydrocarbons fed to the top of the column. Liquid in the bottom of column 52 circulates through line 55 and reboiler 56. Bottoms in column 52 move through line 53 and solvent circulation pump 57 to rich/lean solvent exchanger 47 and then into line 48. An overhead stream of light hydrocarbons leaves the top of column 52 through line 54, is partially condensed in condenser 61, accumulates in reflux accumulator 62, and is split into a liquid fraction and a vapor fraction. The liquid fraction leaves the bottom of reflux accumulator 62 through line 63 and pump 67 to return to the top of column 52 as reflux. Uncondensed hydrocarbons (the vapor fraction), which entered through line 54 with the condensed hydrocarbons, leave accumulator 62 through line 64 and pass through condenser 65 to become liquid $C_2+$ hydrocarbon product.

The overhead stream of nitrogen and methane in line 44 enters second ES column 72, slightly below its middle, to flow upwardly in countercurrent contact with a stream of lean solvent in its extraction section. Liquid in the bottom of column 72 circulates through line 75 and reboiler 76 to be heated. A stream of solvent and methane leaves the bottom of column 72 through line 73 to enter solvent exchanger 77 to be heated. Cooled lean solvent from this exchanger passes through line 78 and solvent cooler 79 to enter the top of column 72. Overhead from column 72 leaves through line 74, passes through optional turbine compressor 71, and becomes the inert gas product.

The heated rich solvent leaves solvent exchanger 77 through line 81 to enter column 82, and liquid in the bottom of column 82 circulates through line 85 and reboiler 86 to be heated. Bottoms in column 82 leave through line 83 and solvent circulation pump 87 to enter solvent exchanger 77 and line 78, to be further cooled in solvent cooler 79 and enter the top of second ES column 72 as lean solvent. The gas flashed or stripped from the incoming liquid in line 81 leaves as overhead through line 84 and optional compressor 88 to become $C_1$ gas product.

Figure 3:
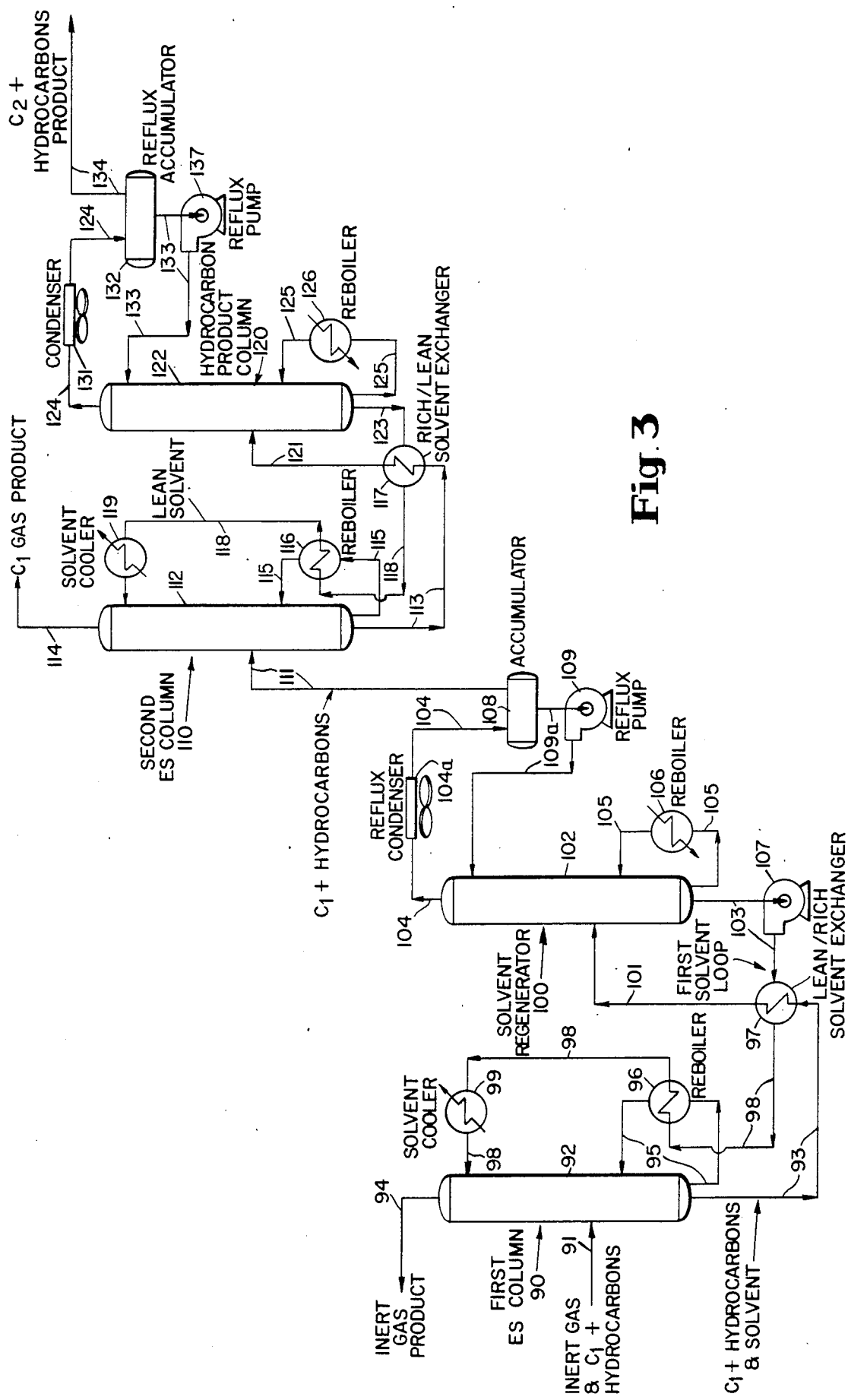
FIG. 3 is a schematic flowsheet showing an extractive stripping process in which the first ES column, as in FIG. 1, separates the inert gas from all of the hydrocarbons and the second ES column separates the methane from the $C_2+$ natural gases.

FIG. 3 illustrates a two-column process in which there is initial separation of the inert gas from all of the hydrocarbon components within the first ES column, as in the process of FIG. 1. This process utilizes a first ES column assembly 90, a solvent regenerator assembly 100, a second ES column assembly 110, and a hydrocarbon product column assembly 120.

Sweet, dry inert gas-containing raw gas enters column 92, slightly below the middle, through line 91. Liquid in the bottom of column 92 circulates through line 95 and reboiler 96 to be heated. Bottoms in column 92 leave through line 93 and solvent exchanger 97. Overhead from column 92 leaves through line 94 as inert gas product.

The heated rich solvent in exchanger 97 passes through line 101 to enter column 102, slightly below its middle. Liquid in the bottom of column 102 circulates through line 105 and reboiler 106 to be heated. Bottoms from column 102 leave through line 103 and pump 107 to enter heat exchanger 97 and pass through line 98, reboiler 96, and solvent cooler 99 to enter the top of first ES column 92 as lean solvent.

An overhead stream leaves column 102 through line 104, is cooled in reflux condenser 104a, enters accumulator 108, and separates into uncondensed and condensed hydrocarbons. The latter leave through line 109a, are pumped by reflux pump 109 to the pressure of column 102, and enter the top of column 102. The uncondensed hydrocarbons leave accumulator 108 through line 111 to enter column 112, slightly below its middle. Liquid in the bottom of column 112 circulates through line 115 and reboiler 116 to be heated. Bottoms leave column 112 through line 113 to enter rich/lean solvent exchanger 117 for heating therein. An overhead stream of $C_1$ gas product leaves the top of column 112 through line 114.

Heated solvent leaves exchanger 117 through line 121 and enters column 122, slightly below its middle. Liquid in the bottom of column 122 circulates through line 125 and reboiler 126 to be heated. Bottoms leave column 122 through line 123, are cooled in exchanger 117, pass through line 118 and reboiler 116, and are further cooled in solvent cooler 119 before entering the top of ES column 112. An overhead stream leaves the top of column 122 through line 124 and is partially condensed in condenser 131 before entering reflux accumulator 132. Condensed liquid in accumulator 132 leaves through line 133 and is pumped by reflux pump 137 to the top of column 122. Uncondensed hydrocarbons in reflux accumulator 132 leave through line 134 to become $C_2+$ hydrocarbons product.

Figure 4:
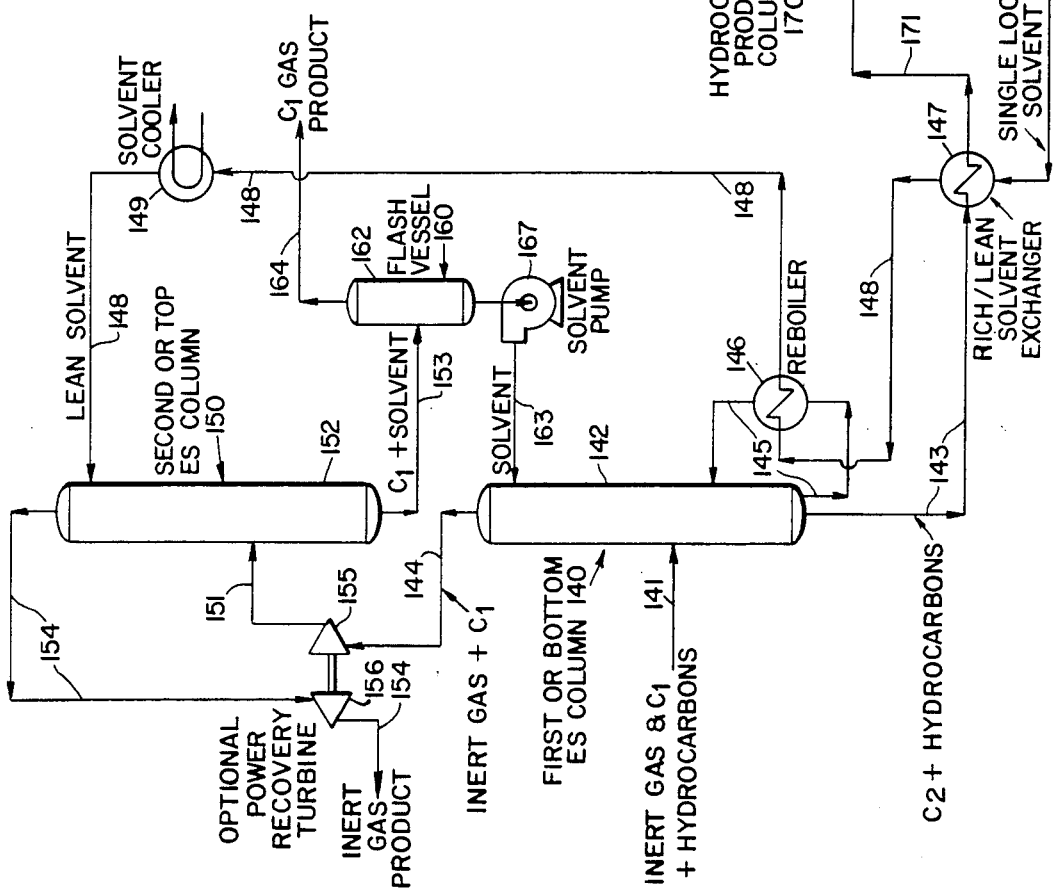
FIG. 4 is a schematic flowsheet illustrating an extractive stripping process in which the first ES column, as in FIG. 2, separates the inert gas plus the methane from the $C_2+$ natural gases which are contained in a rich solvent, and the second ES column separates the inert gas from the methane which is contained in its $C_1$-rich solvent which is fed to a flash vessel and therein is flashed to separate the methane from the solvent which is returned to the top of the first ES column by a solvent pump.

FIG. 4 illustrates an inert gas separation process for an inert gas-containing gas which has been sweetened and dried. The process utilizes a first or bottom ES column assembly 140, a second or top ES column assembly 150, a flash vessel assembly 160, and a hydrocarbon product column assembly 170.

The inlet gas stream in line 141 enters column 142, slightly below it middle, and passes upwardly to meet downwardly descending lean solvent. Liquid in the bottom of column 142 circulates through line 145 and reboiler 146 to be heated. Bottoms in column 142 leave through line 143 to enter and be heated in rich/lean solvent exchanger 147. An overhead stream in line 144 leaves the top of column 142, passes through optional compressor 155 and line 151, and enters column 152, slightly below its middle.

Bottoms leave column 152 through line 153 to enter flash vessel 162, wherein the bottoms are separated into a $C_1$ gas product, which leaves vessel 162 through overhead line 164, and a bottoms which leaves column 162 through line 163 and solvent pump 167 before entering the top of column 142. An overhead stream leaves the top of column 152 through line 154 and passes through optional power recovery turbine 156 to leave as inert gas product. Hot lean solvent leaves exchanger 147 through line 148, passes through reboiler 146, is cooled in solvent cooler 149, and enters the top of column 152.

Heated rich solvent leaves exchanger 147 through line 171 and enters column 172, slightly below its middle. Liquid in the bottom thereof circulates through line 175 and reboiler 176 to be heated. Bottoms leave column 172 through line 173 and are cooled in exchanger 147. An overhead stream leaves through line 174, is condensed by condenser 181, and enters reflux accumulator 182, wherein it is separated into liquid and vapor portions. The liquid portion leaves through line 183 and is pumped by reflux pump 187 to enter the top of column 172. The vapor portion leaves through line 184 to become $C_2+$ hydrocarbon product.

Figure 5:
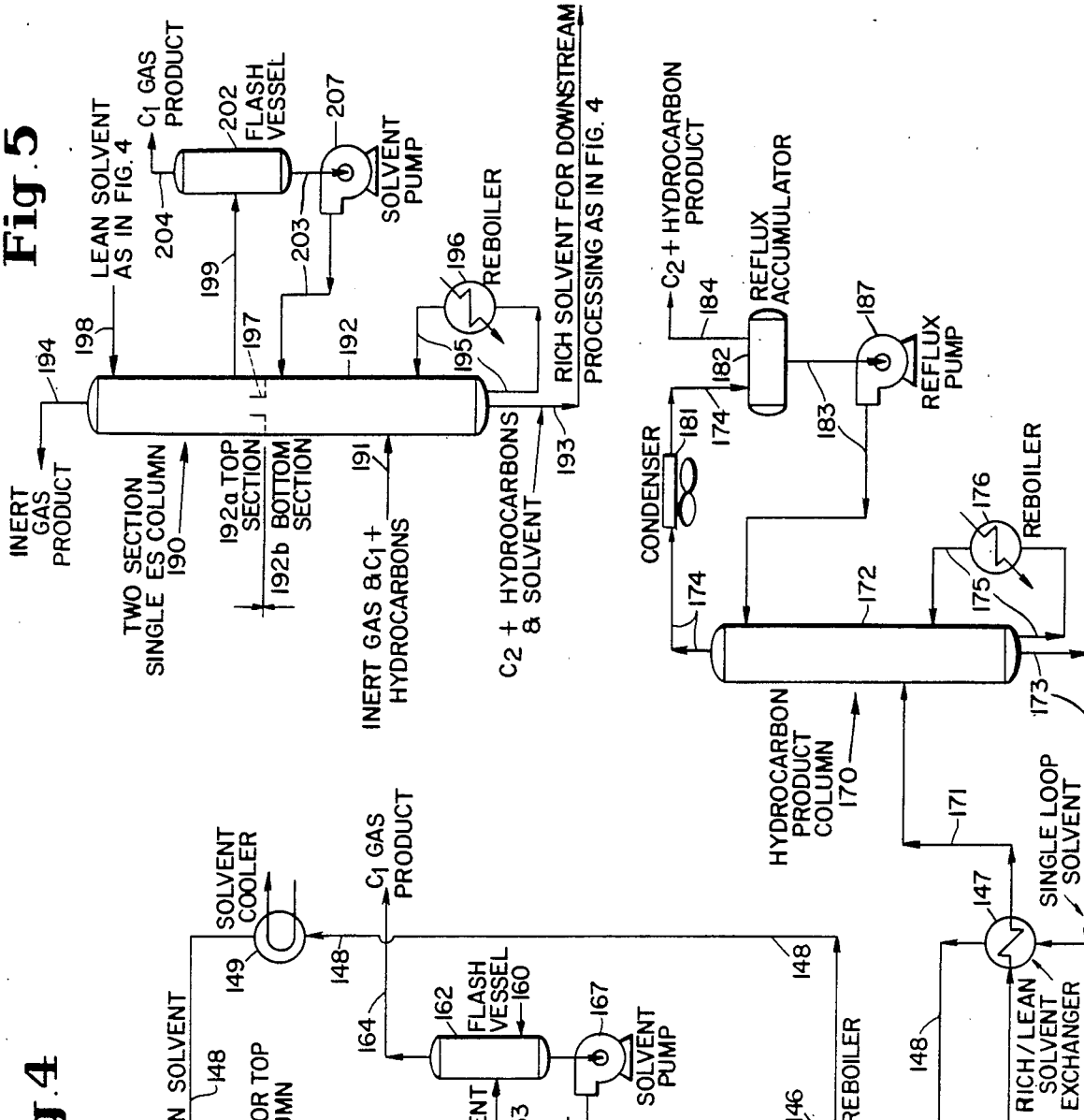
FIG. 5 is a partial schematic flowsheet showing the two ES columns of FIG. 4 built as a single ES column having a top section and a bottom section which are separated by a gas flow-through plate.

FIG. 5 illustrates an alternative embodiment for the two ES columns shown in FIG. 4. These columns are shown to be joined as a single column having a top section and a bottom section. The alternative embodiment comprises two-sectioned column assembly 190 and flash vessel assembly 200. Column assembly 190 comprises column 192 having a top section 192a, a bottom section 192b, and a reboiler 196.

An inert gas-containing raw inlet gas, which has been sweetened and dried, enters the stripping section of bottom section 192b through line 191. Liquid in the bottom of section 192b circulates and is heated by passing through line 195 and reboiler 196. Rich solvent, as bottoms in section 192b, leaves through line 193 to become rich solvent for downstream processing, as in FIG. 4. Rich solvent, as bottoms in top section 192a, leaves through line 199 to enter flash vessel 202 in which it is separated into a $C_1$ gas product which leaves through line 204 and bottoms which leave through line 203 and solvent pump 207 to enter the top of bottom section 192b. Lean solvent enters the top of top section 192a through line 198. An overhead stream of inert gas product leaves the top of top section 192a through line 194.

Because it will be readily apparent to those skilled in the art of treating natural gases that innumerable variations, modifications, applications, and extensions of the examples and principles hereinbefore set forth can be made without departing from the spirit and the scope of the invention, what is hereby defined as such scope and is desired to be protected should be measured, and the invention should be limited, only by the following claims.

What is claimed is:

1. In a process for treating a natural gas stream containing methane, heavier hydrocarbons, and an inert gas,
   an improvement comprising selectively extracting natural gas liquids from said natural gas stream with a preferential physical solvent which provides selective capability for recovery according to said selected degree of: (a) ethane in amounts ranging from 2-98%, (b) propane in amounts ranging from 2-99%, (c) butanes in amounts ranging from 2-100%, or (d) pentanes and higher molecular weight hydrocarbons in amounts ranging up to 100%, said improvement comprising the following steps:
   A. selecting said preferential physical solvent which is selective for ethane and heavier hydrocarbon components of said gas stream such that:
      (1) relative volatility of methane over ethane is at least 5.0 and the hydrocarbon loading capacity, defined as solubility of ethane in said solvent, is at leas 0.25 standard cubic feet of ethane per gallon of said solvent, or
      (2) the preferential factor, determined by the multiplication of relative volatility of methane over ethane by the solubility of ethane in solvent, in standard cubic feet of ethane per gallon of solvent, is at least 1.25;
   B. selectively extracting and stripping said natural gas stream with said physical solvent to produce an inert gas stream and a rich solvent stream containing methane and said hydrocarbons heavier than methane; and
   C. distilling said rich solvent stream to produce a stream of said methane and said selected hydrocarbons heavier than methane and a stream of said physical solvent.

2. In a process for selectively extracting hydrocarbons from a natural gas stream by extractive stripping with a preferential physical solvent which provides selective capability for recovery according to a selected degree of (a) ethane in amounts ranging from 2-98%, (b) propane in amounts ranging from 2-99%, (c) butane in amounts ranging from 2-100%, and (d) pentanes and higher molecular weight hydrocarbons in amounts ranging up to 100%,
   wherein said natural gas stream comprises methane and more than 3 mol. % of an inert gas,
   the improvement which comprises:
   A. selectively extracting and stripping said natural gas stream with said physical solvent to produce: (1) a stream of said methane and said inert gas, and (2) a rich solvent stream containing said selected hydrocarbons heavier than methane, said physical solvent being selective for ethane and heavier hydrocarbon components of said inert gas stream such that: (1) the relative volatility of methane over ethane is at least 5.0 and the hydrocarbon loading capacity, defined as solubility of ethane in solvent, is at least 0.25 standard cubic feet of ethane per gallon of solvent, or (2) the preferential factor, determined by the multiplication of relative volatility of methane over ethane by the solubility of ethane in solvent, in standard cubic feet of ethane per gallon of solvent, is at least 1.25;
   B. distilling said rich solvent stream to produce said selected hydrocarbons heavier than methane and said physical solvent;
   C. extracting and stripping said stream of said methane and said inert gas with a stream of a preferential physical solvent to produce said inert gas as an overhead stream and said methane in a rich solvent stream; and
   D. recovering said methane from said rich solvent stream.

3. In a process for the removal of hydrocarbons heavier than methane from a natural gas stream comprising methane and an inert gas,
   wherein a need exists for recovering said inert gas and separately recovering to any selected degree and at extremely high recoveries a selected hydrocarbon component and heavier hydrocarbons within the group consisting of ethane, propane, butanes, and pentanes, without the need simultaneously to recover hydrocarbons lighter than said selected hydrocarbon component from said natural gas stream,
   the improvement comprising: providing the capability of separately extracting said inert gas and said selected hydrocarbon component and heavier hydrocarbons from said natural gas stream with a preferential physical solvent according to said selected degree of (a) ethane in amounts ranging from 2-98%, (b) propane in amounts ranging from 2-99%, (c) butane in amounts ranging from 2-100%, or (d) pentanes and higher molecular weight hydrocarbons in amounts ranging up to 100% by the following steps:
   A. selectively extracting and stripping said natural gas stream with a stream of a preferential physical solvent, at flow rates within the range of 0.001-0.5 gallon of solvent per standard cubic foot of natural gas, to produce a stream of said inert gas as product and a rich solvent stream containing said methane and said hydrocarbons heavier than methane, said solvent being selective for ethane and heavier hydrocarbon components of said gas stream such that: (1) the relative volatility of methane over ethane is at least 5.0 and the hydrocarbon loading capacity, defined as solubility of ethane in solvent, is at least 0.25 standard cubic feet of ethane per gallon of solvent, or (2) the preferential factor determined by the multiplication of relative volatility of methane over ethane by the solubility of ethane in solvent, in standard cubic feet of ethane per gallon of solvent, is at least 1.25;

B. distilling said rich solvent stream to produce said hydrocarbons as an overhead stream and said physical solvent as a bottoms stream;

C. selectively extracting and stripping said overhead stream of said Step B to produce said selected hydrocarbon component and said heavier hydrocarbon components in a rich solvent stream and said methane in an overhead stream; and D. distilling said rich solvent stream to recover said solvent and produce said selected hydrocarbon components.

4. The process of claims 1, 2 or 3, wherein said contacting of said step A is at 200-1300 psig and wherein said flow rate of said physical solvent is selectively adjusted in response to market conditions.

5. The process of claim 4, wherein additional selectivity is provided by using a reboiler and a stripping section in an extraction column for carrying out said selectively extracting and stripping of said natural gas stream with said preferential physical solvent.

6. The process of claim 5, wherein said additional degree of freedom is effectively utilized by appropriately selecting the reboiling temperature at the bottom of said column in order to produce said rich solvent stream consisting essentially of only said desirable hydrocarbons.

7. The process of claim 6, wherein said stream of undesirable hydrocarbons, flowing upwardly through said stripping section of said column, contains some desirable hydrocarbons which are recovered preferentially by mass transfer principles by transfer to said physical solvent.

8. The process of claim 7, wherein said hydrocarbons, stripped from said rich solvent, leave said stripping section of said column and join the incoming natural gas stream and flow together upwardly within said extraction section of said column, whereby said lean solvent preferentially recovers any contained desirable hydrocarbons.

9. The process of claim 8, wherein said extracting is done in separate extractive stripping (ES) columns.

10. The process of claim 9, wherein a first said ES column produces an inert gas stream, as an overhead stream, and a first rich solvent stream, at a bottoms stream, which is separated into a $C_130$ hydrocarbon stream and a first lean solvent stream by said distilling step.

11. The process of claim 10, wherein said $C_1+$ hydrocarbons stream is fed to a second said ES column which produces a $C_1$ gas product and a second rich solvent stream, containing $C_2+$ hydrocarbons, which is separated into a $C_2+$ hydrocarbons product and a second lean solvent stream by said distilling step.

12. The process of claim 11, wherein said first lean solvent stream and said second lean solvent stream are different solvents.

13. The process of claim 9, wherein a first said ES column produces an overhead mixed stream of said inert gas and said $C_1$ and a first rich solvent stream which is separated into a $C_2+$ hydrocarbon product and a first lean solvent stream.

14. The process of claim 13, wherein said mixed stream is fed to a second said ES column which produces an inert gas stream and a second rich solvent stream.

15. The process of claim 14, wherein said second rich solvent stream is separated into a $C_1$ gas product and a second lean solvent stream.

16. The process of claim 15, wherein said first solvent stream and said second lean solvent stream are different solvents.

17. The process of claim 15, wherein said inert gas stream and said $C_1$ gas product are passed through a power recovery turbine.

18. The process of claim 14, wherein said second rich solvent stream is flashed to produce a $C_1$ gas product stream and a solvent stream which is pumped to the top of said first ES column.

19. The process of claim 18, wherein said inert gas stream and said mixed stream are passed through a power recovery turbine.

20. The process of claim 8, wherein said rich solvent leaving the bottom of said column is let down in pressure to a pressure level that is consistent with the operation of a distillation column for conducting said distilling of said step B.

21. The process of claim 20, wherein said aromatic streams comprise a $C_9$ heart cut or extract of catalytically reformed naphtha which is enriched in $C_9$ alkylbenzenes.

22. The process of claim 21, wherein said $C_9$ aromatics extracted from a naphtha reformate are characterized as having an initial boiling point range of 230°-280° F., an end boiling point range of 350°-425° F., and an API gravity of 35-60.

23. The process of claim 20, wherein said rich solvent is heated before entering said distillation column in order to lower the reboiler heat load on said distillation column.

24. The process of claim 23, wherein said distillation column is a fractionation-type column which separates recovered hydrocarbons from said physical solvent.

25. The process of claim 24, wherein said recovered hydrocarbons leave the top of said distillation column and are condensed to form liquid hydrocarbon product and said lean solvent leaves the bottom of said distillation column.

26. The process of claim 25, wherein the temperature at the bottom of said distillation column is selected to ensure the recovery of all desirable hydrocarbons and is no higher than the boiling point of said physical solvent at said operating pressure.

27. The process of claim 26, wherein said column overhead is refluxed with a portion of said liquid hydrocarbon product in order to minimize loss of said physical solvent with said natural gas liquid product.

28. The process of claim 27, wherein said lean physical solvent is cooled before recycling to said step A as said preferential physical solvent.

29. The process of claim 23, wherein said rich solvent is heated by lean/rich solvent heat exchanging.

30. The process of claim 4, wherein said preferential physical solvent is selected from the group consisting of dialkyl ethers of polyalkylene glycol and streams rich in $C_8-C_{10}$ aromatic compounds having methyl, ethyl, or propyl aliphatic groups.

31. The process of claim 4 wherein said solvent is selected from the group consisting of mesitylene, n-propyl benzene, n-butyl benzene, o-xylene, m-xylene, p-xylene, and mixtures thereof, and aromatic streams rich in mixed xylenes and other $C_8$–$C_{10}$ aromatics.

32. The process of claim 31, wherein said $C_8$–$C_{10}$ aromatic streams are $C_9$ alkylaromatics derived from gasoline producing processes.

33. The process of claim 32, wherein said $C_8$–$C_{10}$ aromatic streams are $C_9$ alkylaromatics derived from conversion of methanol to gasoline.

34. The process of claim 32, wherein said $C_8$–$C_{10}$ aromatic streams are $C_9$ alkylaromatics derived from conversion of syngas to gasoline.

35. The process of claim 31, wherein said $C_8$–$C_{10}$ aromatic streams are $C_9$ alkylaromatics derived from pyrolysis of coal to produce coke.

36. The process of claim 31, wherein said $C_8$–$C_{10}$ aromatic streams are alkylaromatic streams which contain substantial quantities of alkylbenzenes and are produced by petroleum processing operations selected from the group consisting of transalkylation, isomerization, and disproportionation.

37. The process of claim 1, wherein said inert gas is up to 75 mol percent nitrogen.

* * * * *

UNITED STATES PATENT AND TRADEMARK OFFICE
CERTIFICATE OF CORRECTION

PATENT NO. : 4,680,042

DATED : July 14, 1987

INVENTOR(S) : Yuv R. Mehra

It is certified that error appears in the above-identified patent and that said Letters Patent is hereby corrected as shown below:

Column 5, line 41, change "4,617,838" to --4,617,038--.

Claim 1, line 49, change "leas" to --least--.

Claim 10, line 55, change "$C_1 30$" to --$C_1^+$--.

Signed and Sealed this

Eighth Day of December, 1987

Attest:

DONALD J. QUIGG

*Attesting Officer*  *Commissioner of Patents and Trademarks*